United States Patent [19]
Yale

[11] Patent Number: 5,083,922
[45] Date of Patent: Jan. 28, 1992

[54] ABRASIVE LINED PROPHY CUP

[76] Inventor: Joyce K. Yale, 428 31st St., Hermosa Beach, Calif. 90254-2135

[21] Appl. No.: 677,477

[22] Filed: Mar. 29, 1991

[51] Int. Cl.$^5$ ............................................... A61C 3/06
[52] U.S. Cl. .................................................... 433/166
[58] Field of Search ......................... 433/166, 125, 142

[56] References Cited

U.S. PATENT DOCUMENTS

| | | | |
|---|---|---|---|
| 2,226,145 | 12/1940 | Smith | 433/166 |
| 2,738,528 | 3/1956 | Fridge, Sr. | 433/166 |
| 2,789,352 | 4/1957 | Wiseman | 433/166 |
| 3,599,333 | 8/1971 | Muhler | 433/166 |
| 3,789,462 | 2/1974 | Reich | 433/166 |
| 4,447,208 | 5/1984 | Kawai | 433/166 |
| 4,929,180 | 5/1990 | Moreschini | 433/166 |

*Primary Examiner*—Cary E. O'Connor

[57] ABSTRACT

A dental prophylaxis polishing cup of the traditional size, shape, material, and attachments, for use with a rotary dental hand piece. The inside wall of the cavity is provided with an abrasive lining of material such as silicon carbide, arranged in a network pattern, or random pattern, with a narrow, abrasive free margin at the opening edge. The prophylaxis cup is provided in different colors denoting the degree of abrasiveness found inside each different colored prophylaxis cup: blue/coarse, green/medium, grey/fine, and pink/extra-fine.

12 Claims, 1 Drawing Sheet

ABRASIVE LINED PROPHY CUP

BACKGROUND

As part of a dental prophylaxis, the teeth are polished by applying a small rubber cup, commonly called a prophy cup, and pumice paste. The prophy cup is filled or loaded with the pumice paste and then held against the surface of a tooth while being mechanically rotated, e.g. by means of a prophy angle. This forces the pumice paste to abrade across the surface of the tooth, thereby polishing it. The pumice paste commonly comes in granule sizes of coarse, medium, fine, and extra-fine.

A common problem with known devices of this type is the difficulty in retaining the pumice paste within the prophy cup as the cup is being rotated against the tooth. The force of the rotating cup causes the pumice to be thrown away from the tooth making it necessary to refill the prophy cup many times during the prophylaxis procedure. Another common problem with known devices is the difficulty in loading or filling the prophy cup with the pumice paste while performing the dental prophylaxis. A very large problem exists at the receiving end of the dental prophylaxis polishing: the patient's discomfort at having the mouth repeatedly filled with the sandy pumice. Children are particularly vocal in their dislike of this part of the procedure. Many patients are very painfully sensitive to the flavoring agents the manufacturers put in the pumice pastes. To adjust the patient's comfort level, the person performing the dental prophylaxis must stop and have the patient rinse frequently, thereby adding more, and costly, time to the prophylaxis procedure.

A common problem that occurs during the dental prophylaxis is that the dentist or dental hygienist has to use the conventional rubber prophylaxis cup and dip it into a pumice compound numerous times. This means that the patient must rinse the mouth numerous times. But, this portion of the dental prophylaxis may not be eliminated as it is essential to obtain a smooth tooth surface to prevent an otherwise rapid regrowth of unwanted material on the just-scaled tooth. Another problem is that fluoride delivery to the tooth must be done separately, following the pumicing of the teeth, which contributes to longer, non-productive, chair time. Similarly, during gum surgery, it is often desired to polish newly-exposed root surface. This can not be done without introducing a foreign irritant (pumice) into the wound. During the maintenance visits a patient has following gingival surgery, it is undesirable to introduce pumice into a gingival pocket that is to be cleaned and irrigated until such time that it is reduced to an acceptable size. Along with periodontal surgery, these days we have many patients who have dental implants made of metal that are surgically embedded in the jaw bone, with a small portion rising above the gum line. These implants accumulate oral debris but must be treated with great care and delicacy so as not to scratch the metal or introduce pumice into the implant site. Also, practioners find that the pumice dilutes too rapidly in the patient's saliva and is altogether a messy procedure. Another problem with loose pumice is that it invades the prophylaxis angle to which the prophylaxis cup attaches and causes premature wear of the gears.

Regarding dental restorations, a popular acrylic material commonly referred to as "bonding" material, requires a smooth margin or edge. Very often these fillings are very close to the gingiva or gum line and sometimes are placed slightly below the gum line. Up until now, the only smoothing devices have been flat sanding discs on a post driven by a dental handpiece, and sanding strips. The disc can not conform to the curvature of the tooth, nor can it pass beneath the unattached gingiva at the cervical portion of the tooth. The strip can not smooth the convex or concave surface of the tooth. In attempts to use the existing devices, patients have had their tissues cut and torn, but often the fillings just do not get properly finished in order to avoid the resulting tissue trauma.

PROIR ART

A common problem with known devices of the conventional type of prophy cup is that a pumice, in the form of prophy paste, must be added to the cup in order to effect a polished surface.

Another common problem with trying to obtain a polished surface is the brutality to the soft tissue in the mouth of the currently used sanding discs and strips.

Existing prior patents which may be pertinent to the present invention are the following:

Stay Full-easy Load "Turbo" Prophylactic Polishing Cup, U.S. Pat. No. 4,929,180 May 29, 1990 cl 433/166, is a conventional type prophy cup that requires the addition of pumice.

Dental Polisher, U.S. Pat. No. 4,447,208 May 8, 1984 cl 433/166, is not a conventional type prophy cup where the body should be longer and narrower to conform with the required shape and size needed to thoroughly and comfortably contact all available parts of the human tooth. It also is lacking specific and graded abrasive grain sizes to give the operator a choice of finish desired.

Abrasive-Filled Dental Prophylactic Cup, U.S. Pat. No. 3,789,462 Feb. 5, 1974 cl 32/59, is somewhat similar to the traditional type prophy cup in that it has the general shape although it has very short internal capacity. It does have an abrasive lining but it combines large and small grades of abrasive material in the same cup resulting in only large grade abrasive contact with the tooth surface, the large particle overriding the small particle ever making contact with the tooth. This does not allow the operator a choice of particle size. This cup also does not of offer a choice of means of attachment to the dental handpiece. Prior art does not offer a prophy cup long enough to be flexible and manageable.

Dental Prophylaxis Implement, U.S. Pat. No. 3,599,333 Aug. 17, 1971 cl 32/59, is a traditional type prophy cup which requires the addition of pumice.

Tooth Polishing Cup, U.S. Pat. No. 2,789,352 Apr. 23, 1957 cl 32/59, is a prophy cup along the lines of the traditional prophy cup which requires the addition of pumice.

Prophylactic Dental Handpiece, U.S. Pat. No. 2,738,528 Mar. 20, 1956 cl 15/97, is a device known a contra-angle which holds the traditional type prophy cup. In this invention, the contra-angle has a means of supplying the added pumice to the prophy cup, that prophy cup not having any pumice of its own.

Motor Driven Tooth Cleaning Device, U.S. Pat. No. 2,226,145 Dec. 24, 1940 cl 15/29, is a device with the general characteristics of the contra-angle and the traditional prophy cup but dispenses a germicidal agent, and meant for home use, to clean ones teeth where the contemporary toothbrush failed.

SUMMARY OF THE INVENTION

This invention relates to dental devices used to perform the simple but necessary tasks that dentists and dental hygienists need to perform in their day-to-day practice. Rather than trying to make do with the inefficient devices currently available, this invention provides a device specifically related to the performance of the desired task which is to produce a smooth surface on the teeth and their fillings.

According to the invention there is provided a prophy cup for dental use comprising an elongated, hollow body member, attachment means at one end of said body member for fixing the cup to a prophy angle for suitable rotation thereof about the axis of the body member, and an opening at the other end of said body member into a central cavity thereof to provide contact with the tooth surface. This invention provides a prophylaxis cup of the standard rubber-like material and mounted on a prophylaxis angle with a screw, latch, or snap-on friction type attachment. This invention provides that same prophylaxis cup with an abrasive lining of an abrasive nature such as, but not limited to, silicon carbide instead of the traditional webbed, ridged, or smooth, rubber-like material which lines the present prophy cup which requires the addition of pumice paste. This abrasive material will be incorporated into the internal wall of that same prophy cup in a well defined net-like pattern and thereby replace the webbed, ridged, or smooth walls found there in previous prophy cups. There is provided a narrow edge at the open end of the prophy cup to be free of any abrasive material to allow that edge to slide comfortably under the free margin of the gingiva surrounding the cervical portion of the human tooth to be treated. Silicon carbide has been chosen by the manufactures of the acrylic "bonding" type filling materials to be highly efficient in its ability to polish, and very low in undesired abrasiveness.

An object of this invention is to provide the operator a prohy cup with four different degrees of abrasiveness found on the internal cavity of the prophy cup: blue=coarse, green=medium, grey=fine, and pink=extra-fine.

Another object of this invention is to give the dentist and dental hygienist an efficient and comfortable filling smoother and a pumice-less prophylaxis cup. The advantage of having the prophylaxis polishing agent incorporated in the prophy cup where it will not fall out in loose particles will result in savings of both time and effort on the part of the operator performing the prophylaxis procedure. The polishing portion of the prophylaxis can now be done without having to fill the patient's mouth with pumice. The pumice dilutes too rapidly in the patient's saliva, and is altogether a messy procedure. This invention will also eliminate the constant and time consuming rinsing. And now the sensitive patient does not have to tolerate the pain caused by the pumice compounds. Children will no longer object to the polishing of their teeth now that the "sand" has been eliminated. In fact, during the polishing, a fluoride gel can be applied to the teeth, eliminating the need for a whole procedure which follows the polishing, thus saving chair time by combining two procedures into one.

Another object of this invention is to permit a polishing of the exposed root surface during a surgical procedure where it is undesirable to introduce foreign matter such as pumice into the surgical site. An excellent use for this prophylaxis cup is during a follow-up surgical dressing change when careful debridement of the root surface is so important. Also, during the future maintanence visits the post surgical patient has, it is important not to introduce pumice into the gingival pockets, or bone defects adjacent to the teeth, that are to be treated and irrigated in order to reduce their depth to prevent further advancement of periodontal disease. This invention allows the dentist or dental hygienist to carry the polishing of the root surface to any pocket depth desired without fear of inhibiting the benefits of the procedure.

A further object of this invention is to provide a pumice free prophy cup for the delicate maintenance of the dental implant whereby man-made metal roots are surgically embedded in the patient's jaw. The debris that accumulates on these implants must be removed during a dental prophylaxis and the metal must be polished. It is highly desirable not to add pumice into the gum ridges surrounding these implants. This invention, more specifically the extra-fine abrasive prophy cup will render a highly polished surface on the metal and not force any foreign material into the surrounding tissue ridge.

A still further object of this invention is to provide a prophy cup that will conform to the curvatures, convexities, concavities, and unattached subgingival areas of the teeth in order to smooth the rough margins of "bonded" fillings. This flexibility and the well defined layout of the abrasive pattern, along with the choices of abrasive strength, affords the practioner maximum control and ease, and grants the patient comfort and freedom from tissue damage and enamel abrasion while obtaining optimal dental treatment.

Another further object of this invention is to provide a prophy cup which will eliminate having to use loose pumice so as to prevent premature wear on the gears of the prophy angle. Pumice will always find its way into the metal works of the end of the dental handpiece where the prophy cup is attached. It is time consuming to unscrew the parts of the prophy angle, clean them, and oil them. Ideally this should be done before sterilizing them, but then the operator has to contend with contaminated equipment. There is also the saving of considerable amount of money by not having to purchase pumice.

The novel feature which is believed to be characteristic of this invention is the abrasive lining of the prophylaxis cup enabling the operator to fulfill the stated claims. The operator of the dental procedure, the dental prophylaxis or the smoothing of fillings, will have the choice of different abrasive linings of the prophy cups, with different colors to designate coarse lining, medium lining, fine lining, and extra-fine lining.

These and other objects and advantages of this invention will become apparent upon reading the following description of which the attached drawings form a part.

DESCRIPTION OF THE PREFERRED EMBODIMENT

Figure 1:
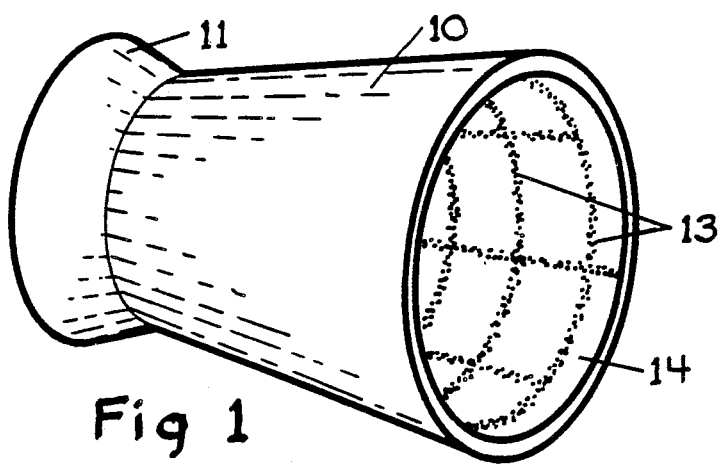
FIG. 1 is a large perspective view of the present invention.

FIG. 1, in a larger scale perspective, shows a dental prophylactic polishing cup, known as a prophy cup, which comprises a truncated conical shaped body portion (10) which is typically made of some flexible material such as rubber or similar material which has elastic properties. A skirt like projection (11) is formed at the screw shank end of the prophy cup which will act, with the aid of centrifugal force, to fling off saliva to protect the gears of the prophy angle from the entrance of salive or other moisture.

Figure 2:
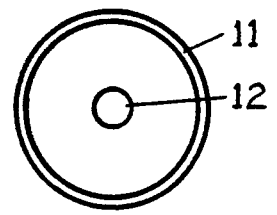
FIG. 2 is a screw shank end view of the present invention.

FIG. 2 shows the attachment (12) end of the prophy cup. For simplicity only prophy cups with a screw shank type of attachment means have been illustrated, but it is to be understood that the invention is also applicable to prophy cups having other means of attaching the cup to the prophy angle, such as the latch type and the snap-on friction type attachments.

Figure 3:
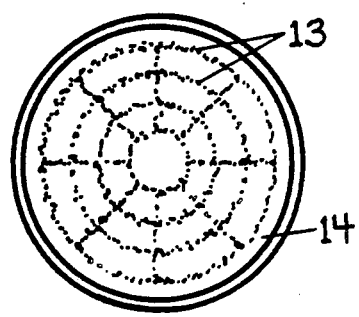
FIG. 3 is the cup opening end view of the present invention.

FIG. 3 is an open end view of the first embodiment showing the abrasive lining (13), also seen in FIG. 1, which is incorporated into the elastic material of the prophy cup with a designated, though not limited to, net pattern, ending in a thin edge without any abrasive material (14), allowing the rim of the prophy cup to fit in and under the free margin of the gingiva surrounding the cervical portion of a human tooth to clean and polish the tooth and/or filling, without irritating or injuring the soft tissue. It is to be understood that other patterns of the abrasive arrangement within the prophy cup are applicable to this invention.

Figure 4:
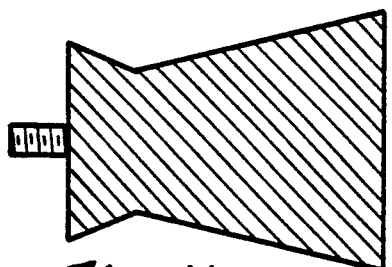
FIG. 4., FIG. 5., FIG. 6., and FIG. 7 are side views of the present invention showing the different textures inside by means of different colors.
Figure 5:
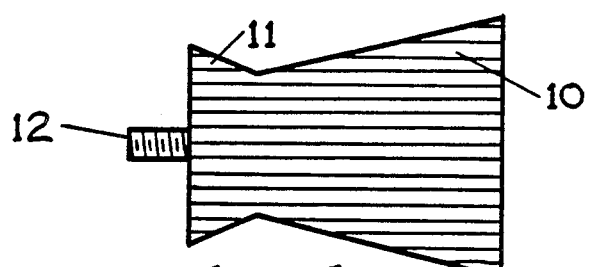
Figure 6:
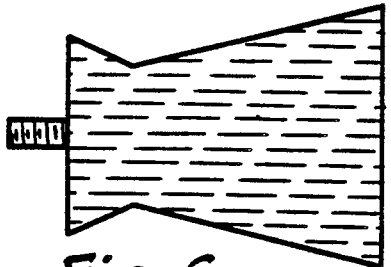
Figure 7:
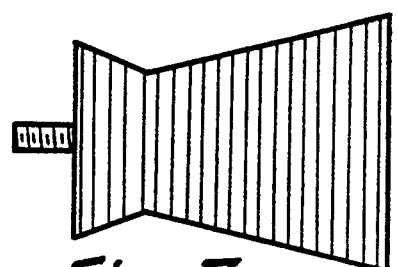

FIGS. 4,5,6, and 7 are side views of four further embodiments of the invention showing a variety of different abrassives available, distinguishable by four different colors. FIG. 4: blue representing coarse abrassive; FIG. 5: green representing medium abrasive; FIG. 6: grey representing fine abrasive; and FIG. 7: pink representing extra-fine. This invention is not limited to, nor confined by, these colors.

Figure 8:
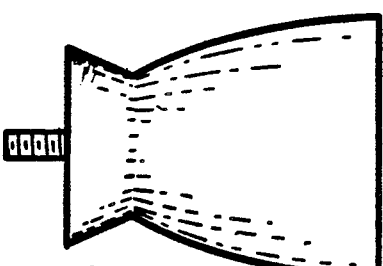
FIG. 8 is a side view of the present invention with a convex shape.

FIG. 8 shows a side view of a prophy cup in accordance with the invention with a convex shaped side so as to better fit the convex portions of the human tooth.

Figure 9:
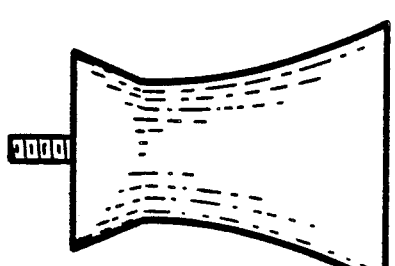
FIG. 9 is a side view of the present invention with a concave shape.

FIG. 9 shows a side view of another prophy cup in accordance with the invention with a concave shaped side so as to better fit the flatter surfaces of the human tooth.

I claim:

1. A prophy cup for dental use with a rotatable prophy angle comprising: an elongated conically shaped body member, attachment means at the smaller end of said body member for fixing the cup to the prophy angle for suitable rotation thereof about the axis of the body member, an opening at the other end of said body member forming a central cavity thereof having an outer circumferential portion, and an abrasive material formed by particles fused to the body member and lining the central cavity of said body member and spaced from the circumferential portion.

2. A prophy cup according to claim 1, wherein the abrasive compound is a silicon carbide type of abrasive.

3. A prophy cup according to claim 1, wherein the attachment means is selected from the group consisting of a screw shank, a latch shank, or a snap-on friction type attachment.

4. A prophy cup according to claim 1, wherein the body member has straight shaped sides.

5. A prophy cup according to claim 1, wherein the body member has convex shaped sides.

6. A prophy cup according to claim 1, wherein the body member has concave shaped sides.

7. A prophy cup according to claim 1, wherein the body member is made of flexible rubber-like material.

8. A prophy cup according to claim 1, wherein the body member has a skirt-like projection at the attaching end for protecting the prophy angle from the entrance of saliva.

9. A prophy cup according to claim 1, wherein individual ones of the prophy cups have different particular colors, each color representing the central cavity lined with a different grade of abrasive material.

10. A prophy cup according to claim 1, wherein the prophy cup has the central cavity lined with the abrasive material arranged in a net-like pattern.

11. A prophy cup according to claim 1, wherein the prophy cup has the central cavity lined with the abrasive material arranged in a random pattern.

12. A prophy cup according to claim 1, wherein the prophy cup has a narrow, abrasive-free margin between the abrasive material network and the edge of the prophy cup at the open end.

* * * * *